United States Patent [19]
Ludwig

[11] Patent Number: 5,484,702
[45] Date of Patent: Jan. 16, 1996

[54] METHOD FOR PRESELECTING RECOMBINANT CLONES CONTAINING A SPECIFIC NUCLEIC ACID SEQUENCE AND SUBSEQUENT TRANSFORMATION WITH PRESELECTED CLONES

[75] Inventor: Linda B. Ludwig, East Aurora, N.Y.

[73] Assignee: Research Foundation of the State University of New York at Buffalo, Amherst, N.Y.

[21] Appl. No.: 189,155

[22] Filed: Jan. 27, 1994

[51] Int. Cl.$^6$ .......................... C07H 21/04; C12P 19/34; C12Q 1/48; C12Q 1/70
[52] U.S. Cl. .................. 435/6; 435/7.1; 435/7.2; 435/7.5; 435/18; 435/71.2; 935/78; 935/81
[58] Field of Search ................... 435/6, 7.1, 7.2, 435/7.5, 18, 91.2; 935/78, 81

[56] References Cited

U.S. PATENT DOCUMENTS

| | | | |
|---|---|---|---|
| 4,656,127 | 4/1987 | Mundy | 435/6 |
| 4,777,129 | 10/1988 | Dattagupta et al. | 435/6 |
| 4,851,331 | 7/1989 | Vary et al. | 435/6 |
| 4,865,967 | 9/1989 | Shiraishi et al. | 435/6 |
| 5,118,605 | 6/1992 | Urdea | 435/6 |

OTHER PUBLICATIONS

Rigas et al., "Rapid plasmid library screening using RecA-coated biotinylated probes", *Proceedings of the National Academy of Sciences USA*, vol. 83, 1986, pp. 9591–9595.
Atkinson, T. et al. Nuc. Acids Res. 16(13):6232, 1988.
Singh, H. et al., Biotechniques 7(3):252–261, 1989.
Zhang, X–k. et al. Nature 355:441–446, 1992.
Hultman, T. et al. J. Biotechnology 35:229–238, 1994 (Jun.).
Kijay, J. M. A. et al. Biotechniques 16(4):657–662, 1994.

*Primary Examiner*—W. Gary Jones
*Assistant Examiner*—Paul B. Tran
*Attorney, Agent, or Firm*—Hodgson, Russ, Andrews, Woods & Goodyear

[57] ABSTRACT

A method for preselecting a nucleic acid sequence of interest is provided. The method comprises immobilizing an affinity molecule to a solid support matrix, wherein the affinity molecule is specific for a hapten or target molecule; hybridization of a "hook" comprised of either an oligonucleotide (complementary to the sequence of interest) labeled with a hapten or target molecule to the target recombinant vector containing the nucleic acid sequence of interest; capturing of the vector-hook via the hapten or target molecule by the respective immobilized affinity molecule for which it has binding specificity; liberating the captured vector DNA by enzymatic digestion of either the hook, or of the immobilized affinity molecule; and adding and incubating competent host cells to promote the introduction of recombinant vector DNA into the competent host cells. Also disclosed are embodiments in which a) the hook is incorporated as part of the vector by hybridization to a denatured vector, followed by second strand synthesis to include the hook as part of the newly synthesized strand; and b) the hook is a protein that binds a genetic element within or adjacent to the nucleic acid sequence of interest, and the immobilized affinity molecule has binding specificity for the protein.

21 Claims, 3 Drawing Sheets

METHOD FOR PRESELECTING RECOMBINANT CLONES CONTAINING A SPECIFIC NUCLEIC ACID SEQUENCE AND SUBSEQUENT TRANSFORMATION WITH PRESELECTED CLONES

BACKGROUND OF THE INVENTION

1. Field of the Invention

This invention relates generally to a method for gene-selection, and more specifically to a method of preselecting a specific recombinant vector containing a nucleic acid sequence of interest from a multitude of different recombinants, and direct introduction of the preselected recombinant vector into a competent host cell.

2. Background and Related Art

The industrial applications of genetic engineering are becoming evident in the production of pharmaceuticals, of foods having improved properties, and of chemical products (including enzymes) to facilitate manufacturing processes. The process of genetic engineering may begin by cloning a gene of interest which encodes a protein with the desired properties for the particular industrial application. Typically, cloning a gene is done by either breaking up a genome into manageable sized fragments, or generating cDNA fragments from isolated m-RNA, and then cloning those genomic or cDNA fragments into a vector and transforming the resultant recombinant vectors into a competent host cell. Commonly used methods for screening transformants, to identify a transformant that contains the recombinant vector with the desired nucleic acid sequence or gene of interest, include a colony-filter lift process where either:

(a) the colonies are lysed on the filter and the filter is screened for the expression of the gene product of interest using monoclonal or polyclonal antisera followed by treatment with a conjugate and subsequent substrate development; or (b) the colonies are lysed onto the filter, and the colony DNA remaining on the filter is denatured and then hybridized to an oligonucleotide probe having incorporated a nonisotopic or isotopic label, wherein the probe is comprised of a nucleic acid sequence complementary to the nucleic acid sequence or gene of interest. Depending on the label incorporated into the probe, the screening process is completed by subjecting the hybridized filter to either substrate development or autoradiography. A modification of this latter technique has been described in U.S. Pat. No. 4,865,967.

However, the cloning of a specific nucleic acid sequence or gene is difficult, tedious, and time-consuming because of the ratio of the occurrence of that sequence or gene relative to the size of the genome or cDNA library to be screened. Thus, in using a colony-filter lift process, usually multiple filters are screened in attempts to identify a single colony containing a recombinant vector with the sequence or gene of interest. Additionally, if screening is done by a method requiring expression of a desired gene product, screening is complicated by the requirements that the gene be expressed in that vector and by the transformed microorganism in a form recognizable by the screening antiserum, and that the expressed gene product is not lethal for the host cell.

A method of physically isolating a recombinant plasmid of interest from a mixture of plasmids has been described (Rigas et al, 1986, *Proc. Natl. Acad. Sci. USA*, 83:9591–9595). In this method, Rec-A was used to form stable complexes between a single-stranded biotinylated probe and the double-stranded DNA molecules sharing sequence homology. Avidin is added to the reaction solution to bind to the probe, and the reaction mixture is chromatographed over cupric iminodiacetic acid agarose beads with a recovery of desired plasmid ranging from 10–20%. A method of preselecting, wherein the loss of preselected nucleic acid is minimized, is desirable.

SUMMARY OF THE INVENTION

The present invention allows for the preselection of a specific recombinant vector containing the nucleic acid sequence or gene of interest from a large number of other recombinant vectors that may be present. The preselection of a recombinant vector containing the desired nucleic acid sequence or gene facilitates the transformation of a host cell and subsequent screening for a transformant containing the preselected vector. The objects of this invention are accomplished by a method comprising (a) immobilizing an affinity molecule to a solid support matrix, wherein the affinity molecule is specific for a hapten or target molecule; (b) specific binding of a "hook" comprised of either an RNA or single-stranded (ss) DNA oligo-nucleotide (complementary to the sequence of interest) labeled with a hapten molecule or target molecule to the respective immobilized affinity molecule for which it has binding specificity; (c) adding to the system a portion of the genomic or cDNA library to be screened wherein the oligonucleotide hook is used to "fish out" the target recombinant vector containing the desired nucleic acid sequence or gene of interest by incubating the system to promote hybridization (complementary base-pairing); (d) washing the support matrix to remove unbound recombinant vector DNA; (e) liberating the captured vector DNA by enzymatic digestion of either the oligonucleotide hook, or of the immobilized affinity molecule; and (f) adding directly to the system competent host cells and incubating/treating the system by any one of several protocols known by those skilled in the art to promote the introduction of recombinant vector DNA into the competent host cells. Note that versatility exists in the system wherein the oligonucleotide hook can be first hybridized to a portion of the genomic or cDNA library to be screened, then the resulting mixture may be added to the solid support matrix containing the immobilized affinity molecules, and the affinity molecules can then "capture" the hook-recombinant vector DNA base-paired complex via the hapten label or target molecule label. The overall scheme of this embodiment method of the present invention is depicted in FIG. 1A wherein biotin is the hapten label, and streptavidin is the immobilized affinity molecule.

In another embodiment of the present invention, the hook labeled with a hapten or target molecule comprises RNA, ssDNA, or double-stranded (ds) DNA complementary to the sequence of interest contained within the cDNA or genomic-DNA vector to be preselected. The vector is denatured (as is the hook if it comprises dsDNA), and the hook is then annealed to the complementary sequence in the denatured vector. The mixture is then used in a polymerase extension reaction containing a highly processive DNA polymerase (modified so that it lacks exonuclease activity) to extend the annealed ss hook in a 5' to 3' direction, thus synthesizing the remainder of the second strand of the denatured vector to which the hook is annealed. The final product is a ds DNA vector containing the sequence of interest, and incorporating the hapten-labeled or target molecule-labeled hook. The label of the hook is then used to immobilize and preselect the recombinant vector. The overall scheme of this embodiment is depicted in FIG. 1B, wherein biotin is the hapten label, and streptavidin is the immobilized affinity molecule.

BRIEF DESCRIPTION OF THE FIGURES

In the accompanying drawings,

FIG. 1 are schematic illustrations briefly summarizing steps used in embodiments of the method of the present invention.

DETAILED DESCRIPTION OF THE INVENTION

Figure 1A:
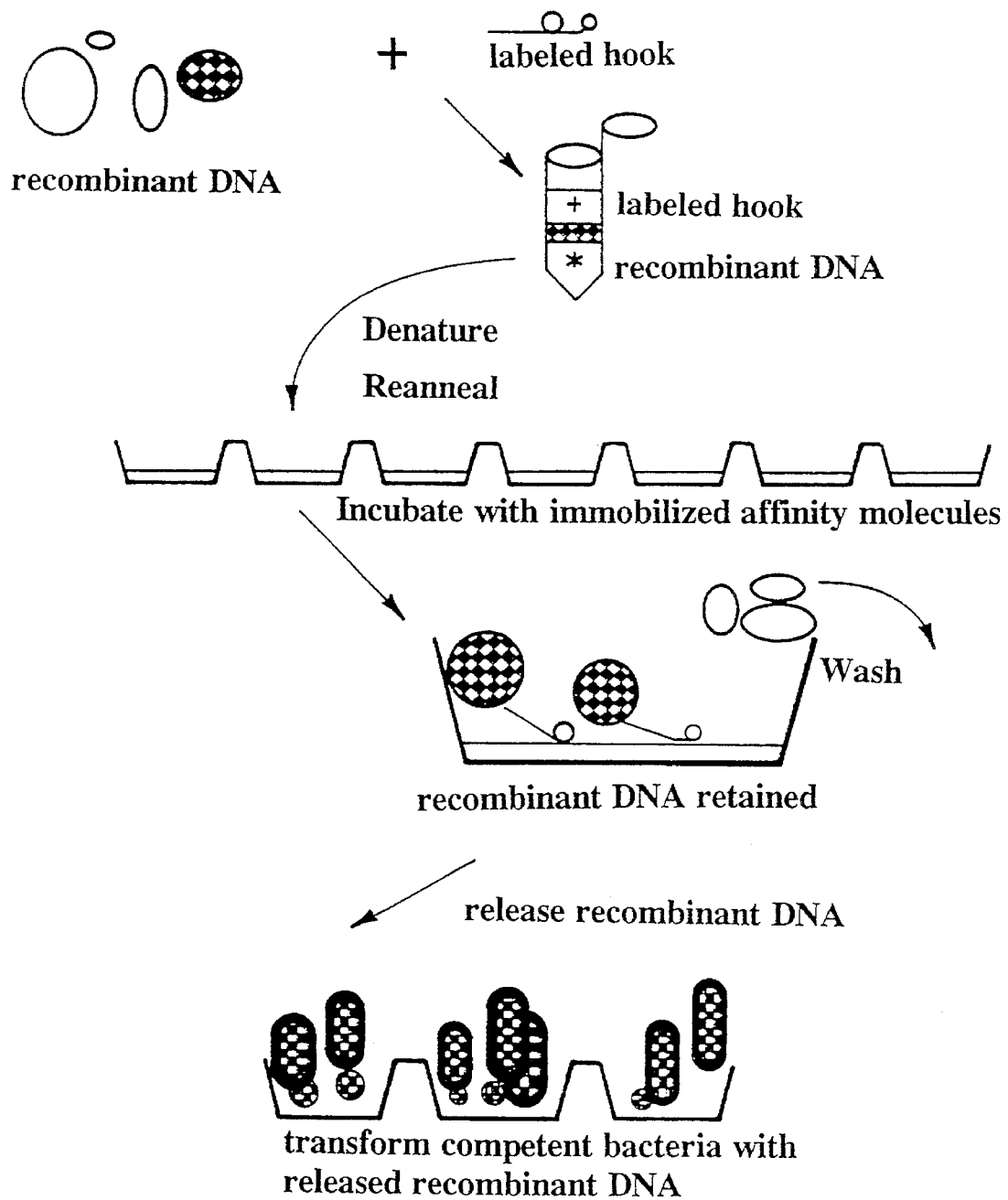
FIG. 1A depicts the embodiment wherein the hook is hybridized to denatured recombinant DNA vectors, and the vector(s) containing the sequence of interest, hybridized to the hook, is then pre-selected by the use of immobilized affinity molecules via binding to the hapten label of the annealed hook. Preselected vector can then be used to transform competent host cells.

The present invention first requires knowing part of the genetic sequence (i.e. minimum 20–30 nucleotides, and up to 100 nucleotides or more) of the gene or nucleic acid sequence of interest to be used as the oligonucleotide in the method of the present invention. Such knowledge, and production of the corresponding oligonucleotides, can be obtained by methods known in the art which include the generation of express sequence tags (ESTs); N-terminal sequencing of the isolated protein of interest and deducing the corresponding nucleic acid sequence; or synthesizing an oligonucleotide which corresponds to a sequence in a conserved region of the gene family of interest, i.e. the gene as isolated from other species wherein conserved sequences are ascertainable by gene bank database analysis.

According to the method of the present invention, the preselection of a specific recombinant DNA-vector depends upon complementary base pairing between the "hook" and the specific recombinant DNA of interest. The term "hook" used herein means an RNA or ssDNA oligonucleotide which is complementary in sequence to the nucleic acid sequence or gene of interest cloned into a recombinant vector. The nature of the hook can be varied in size (nucleotide length), species (RNA or ssDNA), or label (incorporated hapten-labeled or target molecule-labeled nucleotide). The limiting factor is that the hook must contain sufficient complementary base pairs in its sequence to interact with the target recombinant DNA-vector and that it contain a label comprising a hapten or target molecule which will allow specific retention ("capture") of the hook to immobilized affinity molecules on the solid support matrix. By the term "hapten or target molecule" is meant, for the purposes of the specification and claims, molecules useful as molecular labels which are too small to elicit by themselves an immunological response but which are capable of binding with antibodies, and also encompasses small molecules which can serve as molecular labels by virtue of their ability to interact with affinity molecules other than antibodies. By the term "solid support matrix" is meant, for the purposes of the specification or claims, a microtitration plate, vessel, or any series of vessels which may be useful in the practice of the method of the present invention.

In a preferred embodiment, the hook is comprised of either an RNA or ssDNA oligonucleotide, which during synthesis thereof, has incorporated ("is labeled with") biotin-UTP or biotin-dUTP, respectively. When using a biotin-labeled hook (following complementary base pairing with the recombinant DNA-vector) the hook-recombinant DNA vector base-paired complex may then be retained by a streptavidin-coated microtitration well. However, an alternative approach is to label the hook with digoxigenin-11-dUTP (Boehringer Mannheim) and "capture" of the hook-recombinant DNA vector base-paired complex in a microtitration well coated with digoxigenin-specific antibody.

Thus, using the method of the present invention in a microtitration well (of 96-well plates) allows for tremendous versatility and "mass screening." In accordance with the method of the present invention, a specific hook may be utilized to fish out a specific amplified gene product following gene amplification by methods known to those skilled in the art such as polymerase chain reaction. In another embodiment of the present invention, use of a hapten-labeled or target molecule-labeled hook complementary to one set of sequences joined by means of ligase chain reaction (LCR) to an oligonucleotide with a fluorescence label containing the adjacent set of nucleotide sequences for a specific gene such that specific gene analysis is possible in a microtitration well for a) HLA tissue typing; b) screening/detecting rare genes or gene sequence variations involved in the incidence of cancer; c) mass producing screens for specific genetic diseases or infectious diseases (i.e. AIDS), where gene elements are known; and d) detecting serially specific genetic elements (i.e. facilitating the isolation of human genes in the Human Genome Project).

EXAMPLE 1

Coating of microtitration wells of 96-well plates:

The attachment (immobilization) of affinity molecules to plastic can be achieved by non-covalent or covalent means. There are many different protocols known to those skilled in the art to attach affinity molecules such as immunoglobulins, or fragments thereof, to the respective solid surface. Such protocols include preferential adsorption of the Fc portion of the antibody molecules during the coating process, allowing the Fab portion of the anti-body molecules that contain the antigen binding or affinity sites to be more accessible, thus increasing the efficiency of antigen binding in the capture/retention step of the method of the present invention. To prepare the wells for subsequent addition of hapten-labeled or target molecule-labeled hook-recombinant DNA vector base-paired complex, the wells must be washed to remove unbound affinity molecules from the coating process. Nonspecific sites, defined as uncoated surfaces within the well which could bind nonspecifically to components added to the well postcoating, are saturated or blocked to reduce background in the method of the present invention. Blocking agents may be selected from those known in the art including bovine serum albumin (BSA), denatured salmon sperm DNA (optimum concentration of about 20 µg/ml), gelatin, TWEEN-20™, and combinations thereof. The blocking process requires the addition of a solution containing the blocking agent to the wells post-coating, and subsequent incubation for a sufficient time so as to saturate unbound sites. After the blocking process, excess blocking agent is removed by washing the wells with a buffered solution.

The following conditions were found to work well with the method of the present invention. EIA/RIA flat bottom, high binding 96-well plates were coated with 50–100 µl per well of streptavidin at a concentration of 1.4 µg/ml and incubated at 0°–4° C. overnight. Plate wells were then washed twice with PBS and post-coated with 300 µl per well of a blocking solution containing gelatin as previously described (Ludwig et al., 1990, *Mol. Endocrin.* 4:1027–1033) using ethanol precipitated gelatin (Sigma, porcine Type A 300 bloom) am 0.5 mg/ml in PBS for 1 hour at room temperature. The wells were then washed three times with PBS, with a final wash (100 µl per well) of PBS containing 1 µg/ml of RNase/DNase-free BSA and 0.1% NP-40.

Generation of hapten-labeled or target molecule-labeled oligonucleotide hooks

Synthesis of oligonucleotides can be accomplished by any one of several methods known to those skilled in the art. To label an oligonucleotide hook with a hapten or target molecule, hapten-labeled or target molecule labeled dUTP may be added in the process of synthesizing the hook so that the label is incorporated directly into the hook. Alternatively, the label may be incorporated "indirectly" such as by biotinylating the 5' amino group of the hook with sulfo-NHS-biotin. The following conditions and methods have been found to work well in the method of the present invention.

a) biotinylated RNA

Synthesis of RNA, incorporating label such as biotin-UTP, may be performed with DNA-dependent RNA polymerases by using as a template a double-stranded DNA molecule containing the appropriate sequence and bacteriophage SP6, T3 or T7 promoters, as described previously (Molecular Cloning, a laboratory manual: editors Sambrook, Fritsch, Maniatis; Cold Spring Harbor Laboratory Press, 1989).

b) biotinylated DNA (single-stranded)

The polymerase chain reaction may be used to create a ssDNA that contained biotin-dUTP, in essence as described previously (BioTechniques "Producing single-stranded DNA probes with the Taq DNA polymerase: a high yield protocol," 10:36, 1991).

Creation of recombinant cDNA-vector or genomic DNA-vector

Multiple strategies may be employed for incorporating genomic or cDNA into an appropriate vector. The key requirement is that the recombinant genomic DNA or cDNA-vector be capable of transforming bacteria or transfecting eukaryotic cells, and have a selectable marker (i.e. an ampicillin resistance genes or G418 resistance gene, respectively) such that only host cells that take up the recombinant DNA survive when plated for growth on or in media containing the respective selective agent. For example, cDNA may be directionally cloned into a eukaryotic expression vector, such as pRc-CMV (Invitrogen). Inserting the cDNA in the correct orientation in this phagemid vector would allow for subsequent expression of the inserted sequence in eukaryotic cells.

Procedure for preselecting a specific recombinant and then introducing the preselected recombinant into a hose cell in a microtitration well In order to denature the recombinant DNA-vector and then specifically reanneal the recombinant DNA with the hapten-labeled or target molecule labeled hook, separate layer reaction mixtures for each hook:recombinant DNA-vector combination in micro-eppendorf tubes may be set up as follows.

The hapten-labeled or target molecule labeled hook (either RNA or ssDNA) in TE buffer was added to the tube. Then a wax pellet (PECetus, AmpliWax PCR gem) was added and melted am 80° C. for 5 minutes, then cooled to room temperature, such that a hard wax layer overlies the labeled hook. Then, over the hardened wax layer, the recombinant DNA-vector (ligation mixture) was added. The final buffer concentration of the combined layers (mixed upon heating to 80° C.) should consist of 10 mM Tris-Cl, pH 8.3, 50–100 mM KCl, 1.5 mM $MgCl_2$, and 0.001% gelatin. The order of addition of recombinant DNA-vector and labeled hook may be reversed, as long as the wax keeps them separate prior to denaturation, in an effort to prevent false or nonspecific annealing of the oligo-nucleotide (in this case, "false hooking").

Once the three layers are set up in the micro-eppendorf tube (labeled hook; wax; recombinant DNA-vector), the tube(s) are incubated at 94° C. for 5 minutes to denature the DNA and mix the layers. Then, the complementary regions of DNA are allowed to anneal at 60° C. for 5 minutes, and then placed promptly on ice. Variations in these times are possible, as long as the time intervals give ample time for the denaturation of the mixture of the variably-sized recombinant cDNA or genomic DNA ligated into the vector and the subsequent reannealing of complementary labeled hook to the recombinant vector.

At 0°–4° C., aliquots potentially containing labeled hook-recombinant DNA-vector base-paired complexes are then added to the affinity molecule-coated wells and incubated for 30 minutes. The volume per well is not critical, although 10–30 microliters per well has been found to work well with the method of the present invention. Unbound DNA (recombinant DNA-vector not complementary or not bound to the labeled hook) is then removed and the wells are washed twice with TE buffer. Any recombinant DNA-vector "captured" in the well may then be liberated (but not removed from the well) either by treatment with RNase H if the labeled hook was RNA; treatment with mung bean nuclease, if a labeled ssDNA was the hook (at concentrations determined not to affect dsDNA); or alternatively, with a solution containing Proteinase K (10–20 μl of a 250 μg/ml stock) to digest the protein affinity molecule.

The introduction of any preselected recombinant vector present in the well into host cells may be performed by any one of several methods known in the art and depending on the compatible host cell within which the vector is to be introduced. Transformation of competent E. coli may be performed directly in the individual microtitration wells of the 96-well plate(s) potentially containing the pre-selected genomic DNA or cDNA recombinant vectors. Briefly, the following protocol has been found to be useful in the method of the present invention: 1) Vials of frozen competent E. coli (INFaF, Invitrogen) were thawed on iced and the appropriate volume of β-ME was added, tapping gently; 2) To each well containing the preselected DNA, 12 μl of the competent E. coli suspension was added per well, and the wells were mixed by tapping on the side of the 96-well plated followed by incubation of the plate on ice for 30 minutes; 3) The 96-well plate(s) containing the competent E. coli and potentially containing the preselected recombinant DNA-vector were incubated exactly for 60 seconds at 42° C., and then placed on ice for 2 minutes; 4) 100 μl per well of pre-warmed SOC medium was added, and the mixture of medium, preselected DNA and bacteria was transferred to individual, separate culture tubes. An additional 100 μl of medium was added to each well (as wash) and then added to the appropriate, corresponding culture tube. The tubes were incubated at 37° C. for exactly 1 hour with shaking (225 rpm), then placed on ice; and 5) The individual transformation mixtures were then plated on LB agar plates containing ampicillin at 100 μg/ml and incubated over-night at 37° C.

EXAMPLE 2

Preselection of the G3PDH gene and subsequent transformation of the selected clone This embodiment is in accordance with the procedures and methods described in Example 1. To illustrate the method of the present invention, the nucleic acid sequence comprising the G3PDH gene, previously cloned into vector containing a T7 site, was utilized as the DNA template for T7 RNA polymerase. A biotinylated RNA hook, comprising the complementary sequence to the G3PDH cDNA, was synthesized using T7 RNA polymerase, and biotin-21-UTP was incorporated during the synthesis process. A recombinant vector population, composed of the variably sized and unselected cDNA from a heterohybridoma clone B11–12 (Ludwig et al., 1994, Cell. Immunol., in press) directionally cloned into pRc/CMV (Invitrogen), was then hybridized to the biotinylated G3PDH RNA hook according to the methods recited in Example 1. Specifically, the three layers consisting of biotinylated G3PDH RNA hook: wax: ligation mixture of recombinant cDNA-pRc/CMV was incubated at 94° C. for 5 minutes. The complementary regions of DNA were then allowed to anneal at 60° C. for 5 minutes, after which time the hook:cDNA-pRc/CMV recombinant mixtures were incubated on ice. The mixture was then preselected for hook:recombinant DNA-vector base-paired complexes by adding 30 μl aliquots of the mixture per streptavidin-coated well, according to Example 1. After the incubation promoting "capture" of any recombinant DNA complementary to the biotinylated G3PDH RNA hook, and subsequent buffer wash, any DNA captured in the wells was liberated by treatment with RNase H. Competent E. coli were added to the "G3PDH-preselected" cDNA-vector recombinants to each of three wells of a 96-well microtitration plate, and the cells were transformed directly in the wells, according to Example 1. A negative preselection control comprised a biotinylated hook that lacked the binding specificity for the recombinant cDNA-pRc/CMV vector, which was incubated as described for the biotinylated G3PDH RNA hook, wherein the negative preselection control was also used for transforming competent E. coli in wells of the microtitration plate. The three microtitration wells, receiving the G3PDH RNA hook: recombinant cDNA-vector mixtures and then used for transformation of competent E. coli, were used to inoculate (100 μl aliqout from each well) separate LB agar plates containing ampicillin. After overnight incubation at 37° C., the number of colonies counted per plate was 800, 440, and 440 respectively. In contrast, aliquots from the microtitration wells containing the negative preselection control grew only 0–8 colonies per plate. Several colonies were picked at random from each of the 3 plates inoculated with the G3PDH RNA hook:recombinant cDNA-vector transformation mixtures, and the colonies were grown in culture for analysis of the recombinant DNA within the transformants. All of the colonies tested from the G3PDH RNA hook: recombinant cDNA-vector transformation mixture were initially shown to contain G3PDH sequences as determined by the polymerase chain reaction utilizing G3PDH-specific primers.

EXAMPLE 3

Preselection of a sequence in pRc/CMV

Figure 2:
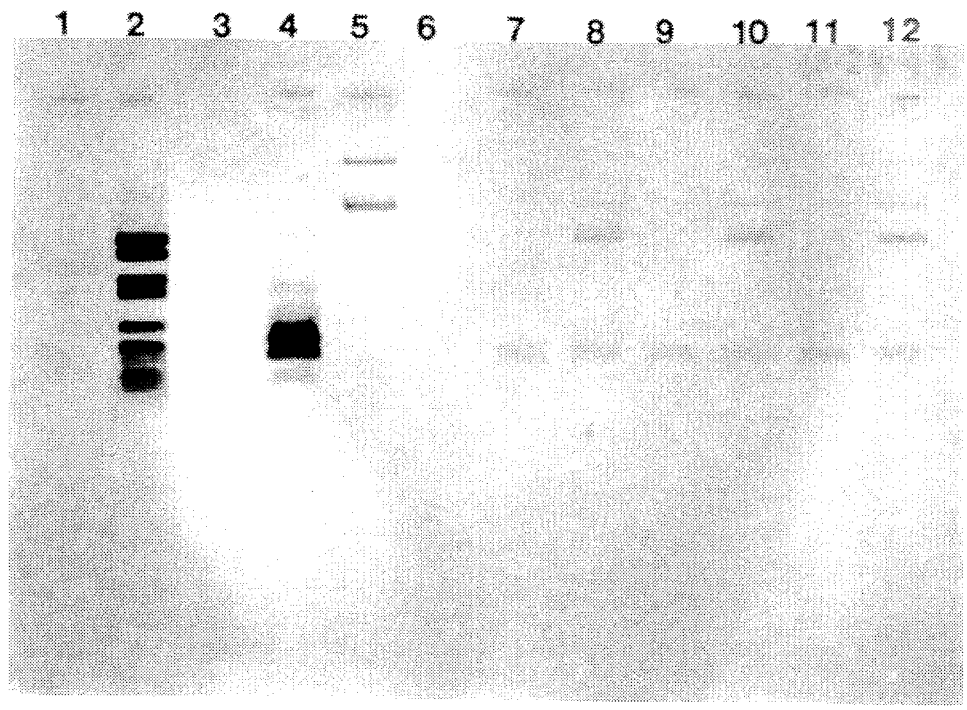
FIG. 2 is a representation of a Southern blot showing the results of preselection reactions according to the method of the present invention. Lane 2 of the membrane contains biotinylated size standards in descending order: 2176 bp, 1766 bp, 1230 bp, 1033 bp, 653 bp, and 517 bp). Positive control lanes are lane 4, containing the biotinylated RNA hook which also was used as the probe; and lane 5, containing 10 ng of pRc/CMV. The contents of the three negative preselection control reactions, i.e. biotinylated RNA hook and pHIV-LTR which were retained in wells after preselection, are shown in lanes 7, 9, and 11. The contents of the preselection reactions containing biotinylated RNA hook and pRc/CMV (containing complementary sequence) which were retained in wells after preselection, are shown in lanes 8, 10, and 12.

This embodiment is in accordance with the procedures and methods described in Example 1. To further illustrate the method of the present invention, the purified nucleic acid sequence comprising the NdeI-ApaI restriction fragment of pRc/CMV, was utilized as the DNA template for T7 RNA polymerase. A biotinylated RNA hook, comprising the complementary sequence to the restriction fragment was synthesized using T7 RNA polymerase, and biotin-21-UTP was incorporated during the synthesis process. Vector pRc/CMV was then hybridized to the biotinylated RNA hook according to the methods recited in Example 1. More particularly, three different denaturing/hybridization conditions, varying only by temperature, were used. Another vector, termed pHIV-LTR and which did not contain the sequences to be preselected, was treated similarly in serving as a negative preselection control. The three different denaturing/hybridization conditions were 94° for 5 minutes/1 minute at 60° C.; 94° for 5 minutes/1 minute at 50° C.; and 94° for 5 minutes/1 minute at 40° C. Each reaction mixture was then preselected by adding an aliquot to a microtitration plate well, which had been coated with streptavidin and postcoated with gelatin, and incubating 1.5 hours at 4° C. After washing the wells, any preselected vector immobilized in the well was released from the streptavidin by digesting the streptavidin with Proteinase K. To monitor the relative efficiency of the preselection method of the present invention, the contents of each well were mixed with loading buffer, and run on agarose gels. The contents in the lanes of the agarose gel were then transferred to a nylon membrane and crosslinked to the membrane. The membrane was hybridized with biotinylated RNA hook, now used as a probe, to detect pRc/CMV in the various preselection reactions performed. Colorimetric detection was accomplished by using strept-avidin-alkaline phosphatase conjugate with subsequent substrate development. FIG. 2 shows the results of the preselection reactions. Lane 2 of the membrane contains biotinylated size standards (in descending order: 2176 bp, 1766 bp, 1230 bp, 1033 bp, 653 bp, and 517 bp).

Positive control lanes are lane 4, containing the biotinylated RNA hook which also was used as the probe; and lane 5, containing 10 ng Df pRc/CMV. The contents of the three negative preselection control reactions, i.e. biotinylated RNA hook and pHIV-LTR (at 94° for 5 minutes/1 minute at 60° C.; 94° for 5 minutes/1 minute at 50° C.; and 94° for 5 minutes/1 minute at 40° C.) which were retained in the wells after preselection, are shown in lanes 7, 9, and 11, respectively. Note only the presence of the biotinylated RNA hook is detected in each of these three lanes. In contrast, the contents of the preselection reactions containing biotinylated RNA hook and pRc/CMV (at 94° for 5 minutes/1 minute at 60° C.; 94° for 5 minutes/1 minute at 50° C.; and 94° for 5 minutes/1 minute at 40° C.) which were retained in the wells after preselection, are shown in lanes 8, 10, and 12, respectively. Note that the pRc/CMV is retained, by the specificity of preselection with the biotinylated RNA hook which hybridized to it because of sequence complementarity. Also present in these three lanes are the biotinylated hook, and a band(s) appearing just below the plasmid bands as they appear for the positive control plasmid. Most likely the additional band represents a different helical twist of the plasmid after the further manipulations of preselection, and/or detection of the triplex structure comprising the ds plasmid to which the RNA hook is still hybridized.

EXAMPLE 4

Preselection by incorporating the hook

Figure 1B:
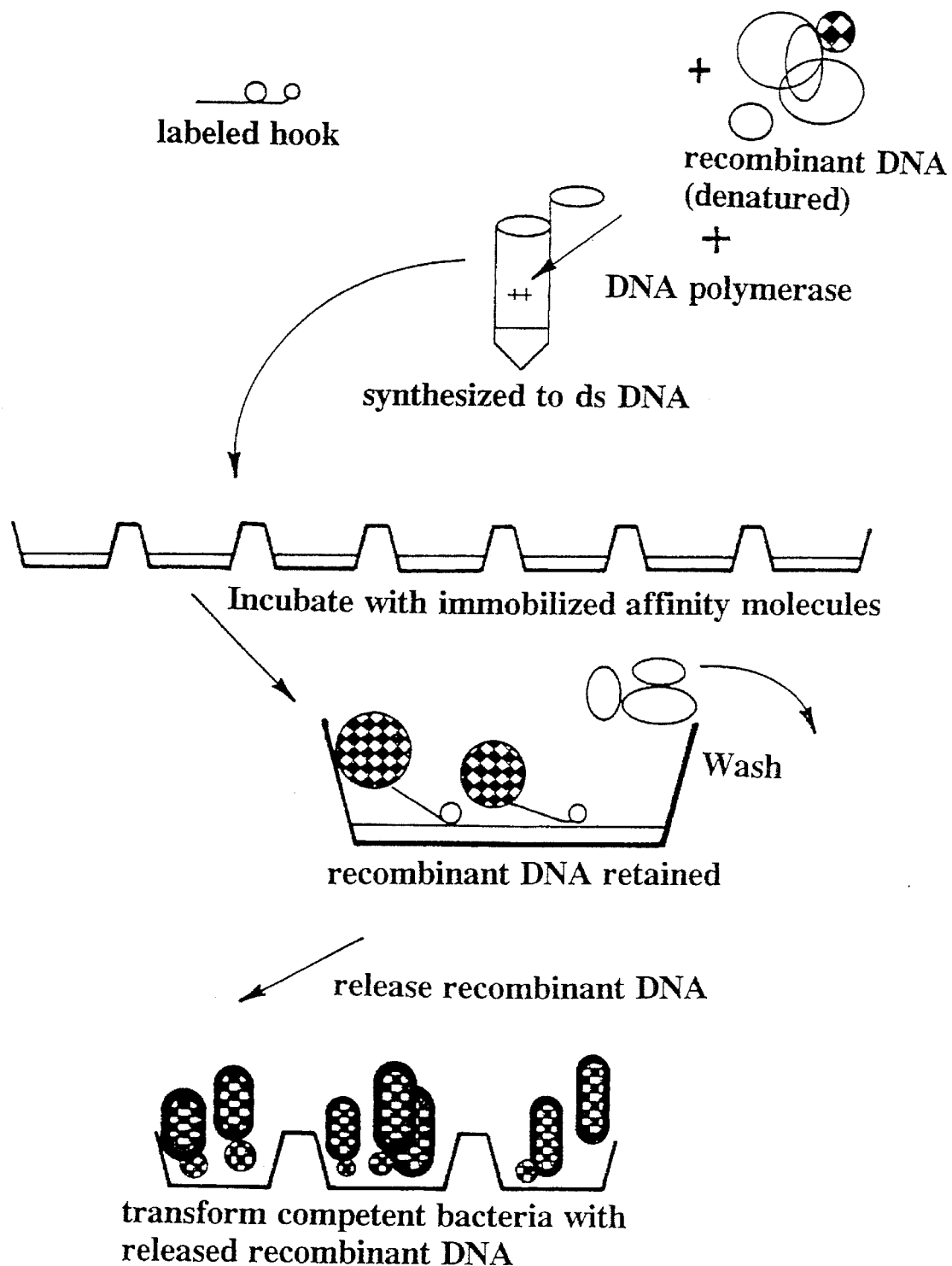
FIG. 1B depicts the embodiment wherein the hook is annealed to denatured recombinant DNA vectors, and the vector(s) containing the sequence of interest, annealed to the hook, is then synthesized to a ds vector by the use of polymerase extension, and preselected for by the use of immobilized affinity molecules via binding to the hapten label of the incorporated hook. Preselected vector can then be used to transform competent host cells.

This embodiment, in part, is in accordance with the procedures and methods described in Example 1. In the previous embodiments, the biotinylated hook is annealed to the complementary sequence contained within the recombinant vector to be preselected, thereby forming a triplex structure (3 strands of nucleic acids). The hook may be synthesized to a nucleic acid sequence of greater than 50–100 base pairs, depending on how much of the target gene sequence is known. In general, the larger the hook, the more stability there is in the triplex structure in manipulations subsequent to the hybridization. However, the particular embodiment described in this example may represent a significant advantage if only a small portion (i.e. 20–25 nucleotides) of a gene sequence is known. In this particular embodiment of the present invention, the hook is annealed to the denatured recombinant vector and the second strand of the recombinant vector is then synthesized by primer extension, resulting in a final product that is the DNA vector containing the sequence of interest having also incorporated the hapten-labeled or target molecule-labeled hook. The remainder of the steps in preselection are described according to the methods and procedures of previous embodiments herein. A brief summary of this particular embodiment is illustrated in FIG. 1B. Thus, only the vectors incorporating the labeled hook will be retained specifically by the immobilized affinity molecules, allowing preselection of a specific cDNA vector or recombinant genomic DNA containing vector out of a ligation mixture such as a library. Since the hook is incorporated as part of the vector to be preselected, inherently there is more stability as compared to the triplex structure formed in previous embodiments herein. Similarly, there is more stability even if a smaller hook is used (i.e. less gene sequence is known) because the labeled hook is incorporated into the recombinant vector to be preselected. In this particular embodiment of the present invention, a highly processive DNA polymerase, modified so that it does not have exonuclease activity (ex. SEQUENASE 2.0$^R$, U.S. Biochemicals) is used to extend the annealed hook in synthesizing the remainder of the second strand of the denatured vector. The hook may comprise either hapten-labeled or target molecule-labeled ssDNA; haphen-labeled or target molecule-labeled RNA; or hapten-labeled or target molecule-labeled synthetic dsDNA provided it is completely denatured prior to the primer-extension reaction with the DNA polymerase.

For purposes of illustration, and not limitation, a portion of vector pRc/CMV was used as a labeled hook. Polymerase chain reaction was used to generate a DNA hook (herein termed the "positive" hook, 152 bp in length) comprising the polylinker sequence between the Sp6 and T7 sites of pRc/CMV. As a negative control DNA hook, polymerase chain reaction was used to generate a 280 bp hook from lambda light chain DNA. Both hooks were dsDNA which incorporated biotinylated nucleotide during their synthesis. pNLgag, not containing the polylinker sequence as present in pRc/CMV, was used as a negative preselection control vector. The two plasmids, and the two hooks, were denatured prior to use by boiling the respective DNA for 10 minutes and then placing them in ice. Different reannealing reactions were set up in this illustration of annealing a hook to the denatured vector, and synthesizing the remainder of the second strand of the denatured vector. One reaction contained 0.5 picomoles of pRc/CMV and 0.25 picomoles of the positive hook. A second reaction 2 contained 0.5 picomoles of pRc/CMV, 0.5 picomoles of pNLgag and 0.25 picomoles of the positive hook. A third reaction contained 0.5 picomoles of pRc/CMV and 0.25 picomoles of the negative control DNA hook. A fourth reaction contained 0.5 picomoles of pRc/CMV and no hook. Reannealing reactions were set up on ice in 20 µl aliquots, heated for 2 minutes at 65° C., and then allowed to cool slowly to room temperature over 30 minutes. The reannealing buffer used for the reactions consisted of 40 mM Tris HCl, pH 7.5, 20 mM MgCl$_2$, and 50 mM NaCl. DNA synthesis reactions, to extend the sequence from annealed hook on the denatured vector, were performed using modified T7 DNA polymerase (SEQUENASE 2.0$^R$). The synthesis reactions were in a final volume of 40 µl and contained dNTPs at a final concentration of 80 µM each, bovine serum albumin at 50 µg/ml, a reaction buffer consisting of 40 mM Tris HCl, pH 7.5, 50 mM NaCl, 10 mM MgCl$_2$, and 5 mM DTT, and 3 units of modified T7 DNA polymerase. The reaction mixtures were incubated at 37° C. for 1 hour, and then the reactions were stopped by heating to 75° C. for 10 minutes. All tubes were allowed to cool to room temperature.

Figure 3:
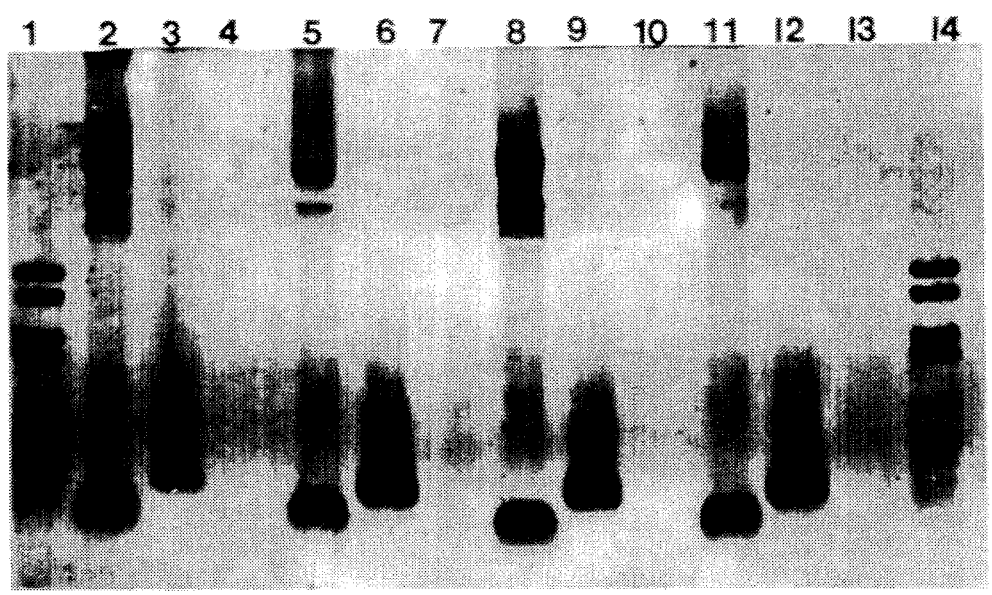
FIG. 3 is a representation of a Southern blot showing the results of preselection reactions according to the another embodiment of the present invention (as schematically illustrated in FIG. 1B). Lanes 1 and 14 of the membrane contains biotinylated size standards; Lanes 2, 5, 8, and 11 contain denatured pRc/CMV template annealed with denatured biotinylated positive hook and then incubated with T7 DNA polymerase; Lanes 3, 6, 9, and 12 contain denatured pRc/CMV template having in the annealing reaction denatured biotinylated negative control hook and then incubated with T7 DNA polymerase; Lanes 4, 7, 10, and 13 contain denatured pRc/CMV template having no biotinylated hook in the annealing reaction and then incubated with T7 DNA polymerase. Lanes 2–7 show the presence of pNLgag DNA in the respective annealing reactions. Lanes 2–4, and 8–10 show synthesis reactions in the presence of single-stranded DNA binding protein.

Prior to preselection of biotinylated, synthesized DNA vector having incorporated the annealed hook, free (unbound) unincorporated biotinylated hook is removed from the vector by size selection chromatography or other methods known to those in the art, so as to prevent the unincorporated hook from competing with the immobilized affinity molecule (in this case, streptavidin) contained in the microtitration well. The contents of synthesis reactions are then preselected in microtitration wells which had been coated with streptavidin, and post-coated with gelatin, in accordance with the methods and procedures of the previous Examples. FIG. 3 illustrates the result of using this particular embodiment to synthesize vector DNA, using ss DNA as a template and a biotinylated hook as a primer, in the presence or absence of noncomplementary DNA (pNLgag). Also the effect of addition of single-stranded DNA binding protein to the synthesis reaction was examined. Following the DNA synthesis reactions, the reaction mixtures were analyzed by agarose gel electrophoresis, Southern transferred to a nylon membrane, and then biotinylated DNA was colorimetrically detected by the use of a streptavidin-alkaline phosphatase conjugate followed by substrate development. Lanes 1 and 14 show biotinylated size standards (in descending order: 2176 bp, 1766 bp, 1230 bp, 1033 bp, 653 bp, 517 bp). Lanes 2, 5, 8, and 11 contain denatured pRc/CMV which was annealed to denatured biotinylated positive hook and then subjected to the DNA synthesis reaction. Lane 2 represents an annealing reaction which additionally included non-complementary DNA pNLgag (excess "junk" DNA), and a synthesis reaction additionally including single-stranded DNA binding protein. Lane 5 represents an annealing reaction which additionally included non-complementary DNA pNLgag, followed by the synthesis reaction. Lane 8 represents a synthesis reaction that additionally included single-stranded DNA binding protein. In comparing lanes 2, 5, 8, and 11, it can be concluded that a) the presence of non-complementary DNA pNLgag (excess "junk" DNA) does not appear to inhibit the annealing and synthesis of the vector containing complementary sequences with the positive hook; and b) single-stranded DNA binding protein appears to improve the yield of biotinylated, synthesized vector incorporating the positive hook.

Lanes 3, 6, 9, and 12 contain denatured pRc/CMV which was placed in an annealing reaction with denatured negative control hook and then subjected to the DNA synthesis reaction. Lane 3 represents an annealing reaction which additionally included non-complementary DNA pNLgag (excess "junk" DNA), and a synthesis reaction additionally including single-stranded DNA binding protein. Lane 6 represents an annealing reaction which additionally included non-complementary DNA pNLgag, followed by the synthesis reaction. Lane 9 represents a synthesis reaction that additionally included single-stranded DNA binding protein. In comparing lanes 3, 6, 9, and 12, it can be concluded that the annealing and synthesis of the vector observed in lanes 2, 5, 8, and 11 is dependent on the specificity (i.e. presence of complementary sequence) of the hook used; i.e., no biotinylated synthesized vector is present unless a positive hook is used.

Lanes 4, 7, 10, and 13 contain denatured pRc/CMV wherein no hook was added in the annealing reaction, but then subjected to the DNA synthesis reaction. Lane 4 represents an annealing reaction which additionally included non-complementary DNA pNLgag (excess "junk" DNA), and a synthesis reaction additionally including single-stranded DNA binding protein. Lane 7 represents an annealing reaction which additionally included non-complementary DNA pNLgag, followed by the synthesis reaction. Lane 10 represents a synthesis reaction that additionally included single-stranded DNA binding protein. In comparing lanes 4, 7, 10, and 13, confirms that the annealing and synthesis of the vector observed in lanes 2, 5, 8, and 11 is dependent on the specificity (i.e. presence of complementary sequence) of the hook used; i.e., no biotinylated synthesized vector is present unless a positive hook is used.

Other modifications of this particular embodiment may become apparent to those skilled in the art from the foregoing example, For instance, disulfide linked-biotin-dUTP can be incorporated into the hook during its synthesis. Retrieval of biotinylated recombinant synthesized vectors from streptavidin-coated wells would then involve only adding DTT (dithiothreitol) to the wells, and no enzymatic digestion of the immobilized affinity molecules would be necessary.

EXAMPLE 5

Preselection of DNA or RNA sequences that bind specifically with its respective binding protein This embodiment of the present invention is similar to embodiments previously described. However, in this embodiment of a method of preselection in a microtitration well, the "hook" used to preselect the desired nucleotide sequence is a protein that interacts with a specific genetic element in that sequence. Alternatively, the specific genetic element may be related to or contiguous with the nucleotide sequence to be selected, and thus by preselecting the specific genetic element, the nucleotide sequence of interest may also be preselected. In this embodiment, a genetic element can include, but is not limited, to an element such as a responsive element, or regulatory element bound by a DNA-binding protein or an RNA-binding protein. The binding protein is a respective protein which specifically, efficiently, and stably binds that particular genetic element. Utilizing buffers and conditions (pH, salt concentration, and temperature) known or determined to be optimal for the nucleotide sequence-binding protein interaction, a recombinant vector population, presumably containing the unselected nucleotide sequence of interest, may be incubated with the respective binding protein having specificity for that sequence or a genetic element associated therewith.

The affinity molecule used for capture is antibody with binding specificity for the binding protein; wherein the antibody may be comprised of polyclonal antisera or monoclonal antibodies. Antibodies useful in this embodiment include those with binding specificity, for the RNA-binding protein or DNA binding protein, that is not inhibited by the nucleotide sequence-binding protein interaction. Likewise, the antibody should not inhibit the binding of the nucleotide sequence to its respective binding protein. If the genetic element or nucleotide sequence to be preselected is comprised of RNA, coating of the microtitration wells with antibody should be done using sterile RNase-free buffers.

To illustrate this embodiment of the method of the present invention, a plasmid containing the DNA element comprising the estrogen-responsive element can be preselected by using the estrogen receptor and anti-estrogen receptor antibody. The antibody may be attached to the microtiter wells by coating the wells in accordance with the procedures and methods described in Example 1. DNA, consisting of a plasmid into which an estrogen-responsive element consensus sequence had been cloned, can be mixed with purified estrogen receptor and incubated for 2.5 hours at 4° C. The reaction mixture consisted of 0.1 volume of DNA in TE buffer (10 mM Tris-HCl and 1 mM EDTA, pH 8.0), and 0.9 vol of estrogen receptor in TDPEK111 buffer (40 mM Tris-HCl, pH 7.5, 1 mM dithiothreitol, 0.5 mM phenylmethylsulfonylfluoride, 1 mM EDTA, and 111 mM KCl, with Nonidet P-40™ at a final concentration of 0.1%). The nucleotide sequence:estrogen receptor mixture is then incubated in anti-estrogen receptor antibody-coated wells to preselect the complexes comprised of DNA containing the estrogen-responsive element bound to estrogen receptor. The time required for the incubation of the nucleotide sequence-binding protein complex with the specific antisera coating the microtitration well is dependent upon the affinity of the antisera for the binding protein, and upon the stability of the nucleotide sequence-binding protein complex formed. For example, when monoclonal antibody to estrogen receptor (such as H222, Abbott Laboratories, North Chicago, Ill.) is used as the affinity molecule, stable binding of the antibody to nucleotide sequence-binding protein complexes may be obtained even after incubation at 4° C. for 14 hours. Plasmids containing the estrogen-responsive element and preselected by this method can then be used to transform bacteria directly in the well following protease treatment of the affinity molecule and/or the binding protein to liberate the plasmids, as described in Example 1. Other methods, such as dissociation by altering the salt concentration, may be used to liberate the nucleotide sequence from its specific binding to the respective binding protein.

In this embodiment, if detection of the complexes is desired in the well, after incubation with affinity molecule but before transformation, either the binding protein or the cloning vectors may be labelled with a marker using methods known in the art for such detection purposes. Additionally, if RNA is preselected with this embodiment of the present invention, the preselected RNA may be first reverse-transcribed into DNA, subsequently inserted into a vector and then introduced into the appropriate host cell.

It should be understood that while the invention has been described in detail herein, the examples were for illustrative purposes only. Other modifications of the embodiments of the present invention that are obvious to those of ordinary skill in the art of molecular biology, medical diagnostics, and related disciplines are intended to be within the scope of the appended claims.

What is claimed is:

1. A method for preselecting a gene or nucleic acid sequence of interest from other DNA, wherein a portion of the nucleic acid sequence of the gene or nucleic acid sequence of interest is known, comprising the steps of:
   (a) immobilizing affinity molecules to a solid support matrix, wherein the affinity molecules are specific for a hapten label or target molecule label;
   (b) hybridizing DNA to be preselected with an oligonucleotide hook complementary to the known portion of the sequence of interest under denaturing and subsequent annealing conditions, said oligonucleotide hook having incorporated hapten label or target molecule label;
   (c) contacting the DNA of step (b) with the immobilized affinity molecules under conditions which promote the specific binding between the affinity molecules and the hapten label or target molecule label of the oligonucleotide hook for which it has binding specificity;
   (d) washing the support matrix to remove unbound DNA; and
   (e) liberating any bound DNA from the solid support matrix by enzymatic digestion of a component selected from the group consisting of the labeled oligonucleotide hook, and the immobilized affinity molecule;
wherein liberated DNA represents the preselected gene or nucleic acid sequence of interest.

2. The method of claim 1, wherein the haphen label is biotin, and the affinity molecules are streptavidin.

3. The method of claim 1, wherein the target molecule label is digoxigenin and the affinity molecules are digoxigenin-specific antibody.

4. The method of claim 1, wherein the oligonucleotide hook is a species selected from the group consisting of RNA, and ssDNA, and asDNA.

5. The method of claim 1, wherein the gene or nucleic acid sequence of interest is contained within a recombinant DNA vector, and further comprising
   introducing the liberated DNA, containing said recombinant vector, into a competent host cell.

6. The method of claim 1, wherein the immobilized affinity molecules are attached to solid support matrix by covalent or noncovalent means.

7. The method of claim 6, wherein solid support matrix is treated after attachment of the affinity molecules so as to prevent non-specific binding of added DNA to areas of the matrix not bound by affinity molecules.

8. A method for preselecting a gene or nucleic acid sequence of interest from other nucleic acids, wherein a portion of the nucleic acid sequence of the gene or nucleic acid sequence of interest contains a genetic element that binds specifically to a binding protein, comprising the steps of:
   (a) immobilizing affinity molecules to a solid support matrix, wherein the affinity molecules have binding specificity for the binding protein which does not inhibit, or is not inhibited by, binding between the binding protein and the genetic element;
   (b) incubating the nucleic acid sequence containing the genetic element with a binding protein known to specifically bind to said genetic element under incubation conditions that promote specific binding;
   (c) contacting the nucleic acid sequence and binding protein mixture of step (b) with the immobilized affinity molecules under conditions which promote the specific binding between the affinity molecules and the binding protein for which it has binding specificity;
   (d) washing the support matrix to remove unbound nucleic acid sequences; and
   (e) liberating any nucleic acid sequence bound to the binding protein by dissociation, or by enzymatic digestion of a component selected from the group consisting of the binding protein, and the immobilized affinity molecule, or a combination of both;
wherein liberated nucleic acid sequence represents the preselected gene or nucleic acid sequence of interest containing the genetic element.

9. The method of claim 8, wherein the genetic element is related to or contiguous with the gene or nucleic acid sequence of interest.

10. The method of claim 8, wherein the genetic element is an element bound by a protein selected from the group consisting of a DNA-binding protein and a RNA-binding protein.

11. The method of claim 8, wherein the affinity molecules are selected from the group consisting of polyclonal antibodies and monoclonal antibody, or a combination thereof.

12. The method of claim 8, wherein the immobilized affinity molecules are attached to solid support matrix by covalent or noncovalent means.

13. The method of claim 8, wherein solid support matrix is treated after attachment of the affinity molecules so as to prevent non-specific binding of added nucleic acid sequences to areas of the matrix not bound by affinity molecules.

14. The method of claim 8, wherein the gene or nucleic acid sequence of interest is contained within a recombinant DNA vector, and further comprising
   introducing liberated DNA, containing said recombinant vector, into a competent host cell.

15. A method for preselecting a gene or nucleic acid sequence of interest from other DNA, wherein a portion of the nucleic acid sequence of the gene or nucleic acid sequence of interest is known, comprising the steps of:
   (a) immobilizing affinity molecules to support matrix, wherein the affinity molecules are specific for a hapten label or target molecule label;
   (b) denaturing DNA to be preselected and annealing the denatured DNA with a single-stranded oligonucleotide hook complementary to the known portion of the sequence of interest, said oligonucleotide hook having incorporated hapten label or target molecule label;

(c) synthesizing a second strand of the DNA containing the sequence of interest by an extension reaction, from the annealed labeled hook, containing a DNA polymerase which lacks exonuclease activity, wherein the labeled hook becomes incorporated as part of the synthesized double-stranded DNA;

(d) removing unannealed hook from labeled, synthesized double-stranded DNA of step (c);

(e) contacting the labeled, synthesized double-stranded DNA of step (d) with the immobilized affinity molecules under conditions which promote the specific binding between the affinity molecules and the hapten label or target molecule label in the synthesized DNA for which it has binding specificity;

(f) washing support matrix to remove unbound DNA; and (g) liberating any bound DNA from solid support matrix by enzymatic digestion, or chemical dissociation of a component selected from the group consisting of the labeled oligonucleotide, and the immobilized affinity molecule;

wherein liberated DNA represent the preselected gene or nucleic acid sequence of interest.

16. The method of claim 15, wherein the hapten label is biotin, and the affinity molecules are streptavidin.

17. The method of claim 15, wherein the target molecule label is digoxigenin and the affinity molecules are digoxigenin-specific antibody.

18. The method of claim 15, wherein the oligonucleotide hook is a species selected from the group consisting of RNA, and ssDNA, and dsDNA.

19. The method of claim 15, wherein the gene or nucleic acid sequence of interest is contained within a recombinant DNA vector, and further comprising a step selected from the group consisting of (a) introducing liberated DNA, containing said recombinant vector, into a competent host cell; and (b) further analyzing the sequence of the gene or nucleic acid of interest contained in the liberated DNA.

20. The method of claim 15, wherein the immobilized affinity molecules are attached to solid support matrix by covalent or noncovalent means.

21. The method of claim 20, wherein solid support matrix is treated after attachment of the affinity molecules so as to prevent non-specific binding of added DNA to areas of the matrix not bound by affinity molecules.

* * * * *

UNITED STATES PATENT AND TRADEMARK OFFICE
CERTIFICATE OF CORRECTION

PATENT NO. : 5,484,702
DATED : January 16, 1996
INVENTOR(S) : Ludwig

It is certified that error appears in the above-identified patent and that said Letters Patent is hereby corrected as shown below:

Column 1,
Line 6, please insert in the first paragraph:
-- This invention was made with Government support under Grant No. R01 MH47225 awarded by the National Institutes of Health. The Government has certain rights in the invention --.

Signed and Sealed this

Nineteenth Day of August, 2003

JAMES E. ROGAN
*Director of the United States Patent and Trademark Office*